United States Patent
Rusin et al.

(10) Patent No.: US 7,551,963 B2
(45) Date of Patent: Jun. 23, 2009

(54) APPARATUS TO IMPROVE THE HIGH VOLTAGE FLASHOVER CHARACTERISTICS OF EMI FEEDTHROUGH FILTERS USED IN ACTIVE IMPLANTABLE MEDICAL DEVICES

(75) Inventors: Robert Rusin, Clarence, NY (US); Christine A. Frysz, Marriottsville, MD (US); Robert A. Stevenson, Canyon Country, CA (US)

(73) Assignee: Greatbatch Ltd., Clarence, NY (US)

( * ) Notice: Subject to any disclaimer, the term of this patent is extended or adjusted under 35 U.S.C. 154(b) by 560 days.

(21) Appl. No.: 11/160,712

(22) Filed: Jul. 6, 2005

(65) Prior Publication Data
US 2006/0173506 A1 Aug. 3, 2006

Related U.S. Application Data

(60) Provisional application No. 60/648,935, filed on Feb. 1, 2005.

(51) Int. Cl.
*A61N 1/375* (2006.01)
(52) U.S. Cl. ....................................................... 607/37
(58) Field of Classification Search ............... 361/4, 361/12; 607/36, 37
See application file for complete search history.

(56) References Cited

U.S. PATENT DOCUMENTS

| | | | | |
|---|---|---|---|---|
| 3,931,456 A | * | 1/1976 | McChesney, Jr. | 174/145 |
| 3,988,565 A | * | 10/1976 | Hill | 219/121.11 |
| 4,514,207 A | | 4/1985 | Klye | |
| 5,177,663 A | * | 1/1993 | Ingleson et al. | 361/321.2 |
| 5,333,095 A | | 7/1994 | Stevenson et al. | |
| 5,825,608 A | * | 10/1998 | Duva et al. | 361/302 |
| 6,349,025 B1 | | 2/2002 | Fraley et al. | |
| 6,510,038 B1 | | 1/2003 | Satou et al. | |
| 6,529,103 B1 | | 3/2003 | Brendel et al. | |
| 7,260,434 B1 | * | 8/2007 | Lim et al. | 607/37 |
| 2003/0040779 A1 | * | 2/2003 | Engmark et al. | 607/36 |

FOREIGN PATENT DOCUMENTS

| EP | 0331959 | 9/1989 |
|---|---|---|
| WO | 9712645 | 4/1997 |

* cited by examiner

*Primary Examiner*—Scott M Getzow
(74) *Attorney, Agent, or Firm*—Kelly Lowry & Kelley, LLP

(57) ABSTRACT

A feedthrough terminal assembly for an active implantable medical device includes a conductive terminal pin or leadwire, a feedthrough filter capacitor having a first set of electrode plates conductively coupled to the terminal pin or leadwire, and a second set of electrode plates conductively coupled to a housing, ferrule or ground plane of the active implantable medical device, and a non-conductive mullion disposed relative to the terminal pin or leadwire for increasing creepage distance between the terminal pin or leadwire and another conductive element, creating a tortuous path that increases resistance to arcing/flashover.

21 Claims, 3 Drawing Sheets

BODY FLUID SIDE

APPARATUS TO IMPROVE THE HIGH VOLTAGE FLASHOVER CHARACTERISTICS OF EMI FEEDTHROUGH FILTERS USED IN ACTIVE IMPLANTABLE MEDICAL DEVICES

The above identified application claims priority on U.S. Provisional Patent Application No. 60/648,935 filed Feb. 1, 2005.

BACKGROUND OF THE INVENTION

The present invention relates generally to EMI filter assemblies, particularly of the type used in active implantable medical devices (AIMDs) such as cardiac pacemakers, cardioverter defibrillators and the like. More particularly, the present invention relates to a filter assembly with increased resistance to arcing/flashover.

Feedthrough terminal pin assemblies are generally well known in the art for use in connecting electrical signals through the housing or case of an electronic instrument. For example, in implantable medical devices such as cardiac pacemakers, defibrillators and the like, the terminal pin assembly comprises one or more conductive terminal pins supported by an insulator structure for feedthrough passage of electrical signals from the exterior to the interior of the medical device. Many different insulator structures and related mounting methods are known for use in medical devices wherein the insulator structure provides a hermetic seal to prevent entry of patient body fluids into the medical device housing, where such body fluids could otherwise interfere with the operation of and/or cause damage to internal electronic components of the medical device.

In the past, two primary technologies have been employed to manufacture the hermetic seal. One technique involves the use of an alumina insulator which is metallized to accept brazing material. This alumina insulator is brazed to the terminal pin or pins, and also to an outer metal ferrule of titanium or the like. The alumina insulator supports the terminal pin or pins in insulated spaced relation from the ferrule which is adapted for suitable mounting within an access opening formed in the housing of the medical device. In an alternative technique, the hermetic seal comprises a glass-based seal forming a compression or matched fused glass seal for supporting the terminal pin or pins within an outer metal ferrule.

The feedthrough terminal pins are typically connected to one or more leadwires which, in the example of a cardiac pacemaker, sense signals from the patient's heart and also couple electronic pacing pulses from the medical device to the patient's heart. Unfortunately, these leadwires can act as an antenna to collect stray electromagnetic interference (EMI) signals for transmission via the terminal pins into the interior of the medical device. Such unwanted EMI signals can disrupt proper operation of the medical device, resulting in malfunction or failure. For example, it has been documented that stray EMI signals emanating from cellular telephones can inhibit pacemaker operation, resulting in asynchronous pacing, tracking and missed beats. To address this problem, hermetically sealed feedthrough terminal pin assemblies have been designed to include a feedthrough capacitor for decoupling EMI signals in a manner preventing such unwanted signals from entering the housing of the implantable medical device. See, for example, U.S. Pat. Nos. 4,424,551; 5,333,095; 5,751,539; 5,905,627; 5,973,906; 6,008,980; and 6,566,978. These prior art feedthrough capacitor EMI filters generally provide a high degree of attenuation to EMI in the frequency range between 450 and 3000 MHz.

Accordingly, there is a need for circuit protection devices which will improve the immunity of active implantable medical device systems to diagnostic procedures such as MRI. There is also a need to provide increased filtering for AIMD's due to the recent proliferation in the marketplace of new higher power emitters. These include aftermarket cellular telephone amplifiers, associated higher gain antennas and radio frequency indentification (RFID) readers and scanners. The present invention fulfills all of these needs and provides other related advantages.

SUMMARY OF THE INVENTION

The present invention resides in a feedthrough terminal assembly for an AIMD including a conductive terminal pin or leadwire.

The feedthrough terminal assembly is specifically designed for use with active implantable medical devices including a cardiac pacemaker, an implantable defibrillator, a congestive heart failure device, a hearing implant, a neurostimulator, a drug pump, a ventricular assist device, an insulin pump, a spinal cord stimulator, an implantable sensing system, an artificial heart, an incontinence device, a bone growth stimulator, a gastric pacemaker, or a prosthetic device.

In the novel feedthrough terminal assembly described herein, a feedthrough filter capacitor has a first set of electrode plates conductively coupled to the terminal pin or leadwire, and a second set of electrode plates conductively coupled to a housing, ferrule or ground plane of the active implantable medical device.

A non-conductive mullion is disposed relative to the terminal pin or leadwire for increasing creepage distance between the terminal pin or leadwire and another conductive element, creating a tortuous path that increases resistance to arcing/flashover.

A second conductive terminal pin or leadwire extends through the feedthrough filter capacitor such that at least a portion of the mullion is disposed between the conductive terminal pins or leadwires. The mullion is disposed adjacent to the capacitor and adhesively connected thereto.

The capacitor and the mullion are at least partially housed within a ferrule.

The mullion comprises a disc having apertures through which the terminal pins or leadwires extend. The disc includes an extension for separating the terminal pins or leadwires from one another and the extension has convolutions for increasing creepage distance.

Other features and advantages of the present invention will become apparent from the following more detailed description, taken in conjunction with the accompanying drawings which, by way of example, illustrate the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
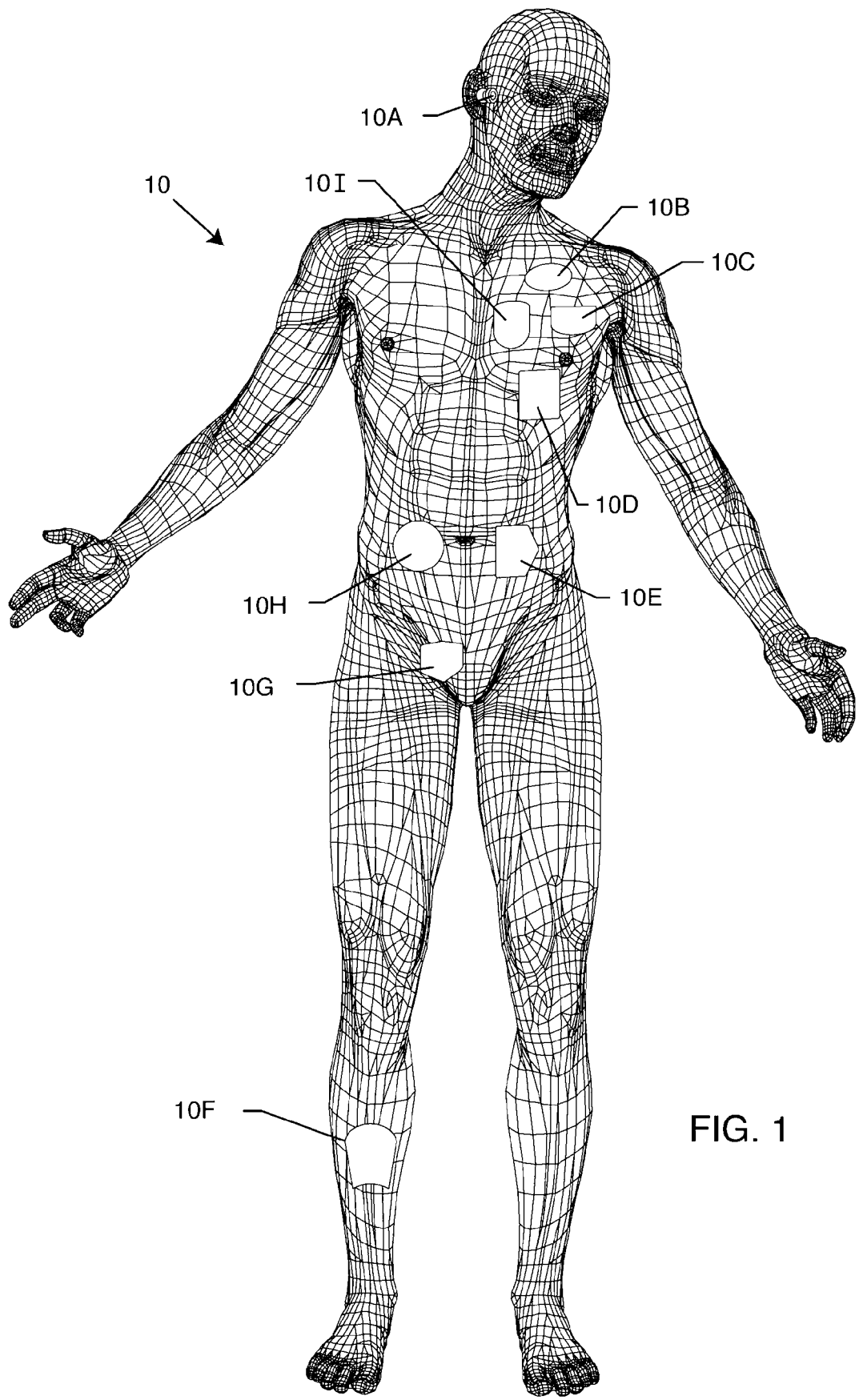
FIG. 1 is a schematic illustration of a human body illustrating various types of AIMD's currently in use.

FIG. 1 is an example of the various types of active implantable medical devices 10 currently in use. FIG. 1 is a wire formed diagram of a generic human body showing a number of implanted medical devices. 10A is a family of hearing devices which can include the group of cochlear implants, piezoelectric sound bridge transducers and the like. 10B includes an entire variety of neurostimulators and brain stimulators. Neurostimulators are used to stimulate the vegas nerve for example to treat epilepsy, obesity and depression. Brain stimulators are similar to a pacemaker-like device and include electrodes implanted deep into the brain for sensing the onset of the seizure and also providing electrical stimulation to brain tissue to prevent the seizure from actually happening. 10C shows a cardiac pacemaker which is well-known in the art. 10D includes the family of left ventricular assist devices (LVAD's), and artificial hearts, including the recently introduced artificial heart known as the Abiocor. 10E includes an entire family of drug pumps which can be used for dispensing of insulin, chemotherapy drugs, pain medications and the like. 10F includes a variety of bone growth stimulators for rapid healing of fractures. 10G includes urinary incontinence devices. 10H includes the family of pain relief spinal cord stimulators and anti-tremor stimulators. Insulin pumps are evolving from passive devices to ones that have sensors and closed loop systems. That is, real time monitoring of blood sugar levels will occur. These devices tend to be more sensitive to EMI than passive pumps that have no sense circuitry. 10H also includes an entire family of other types of neurostimulators used to block pain. 10I includes a family of implantable cardioverter defibrillators (ICD) devices and also includes the family of congestive heart failure devices (CHF). This is also known in the art as cardio resynchronization therapy devices, otherwise known as CRT devices.

Figure 2:
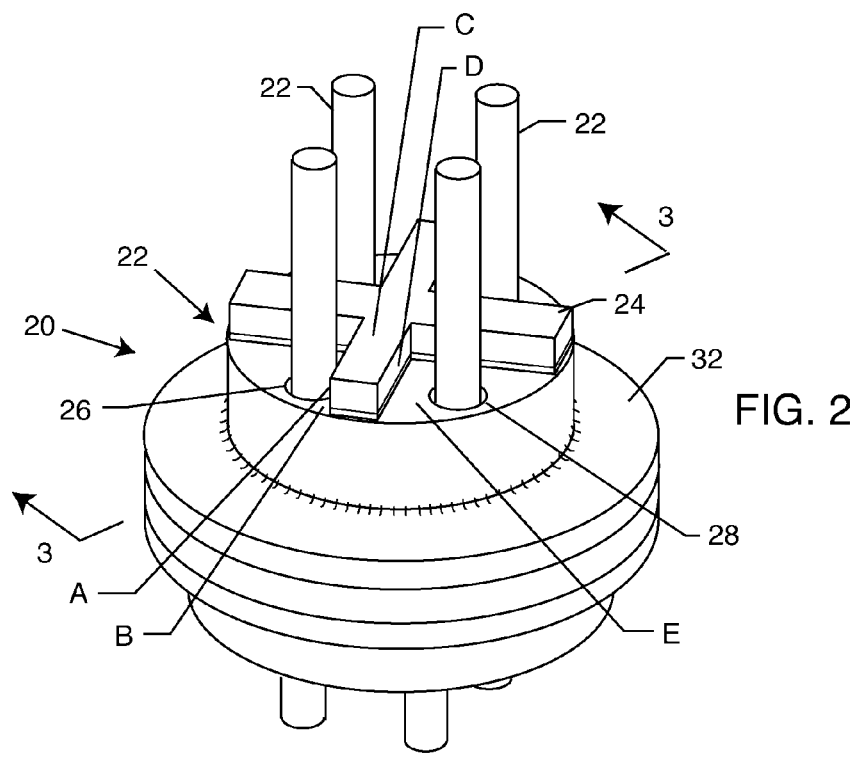
FIG. 2 is a perspective view of a feedthrough terminal assembly with a mullion embodying the present invention on a top surface thereof.
Figure 3:
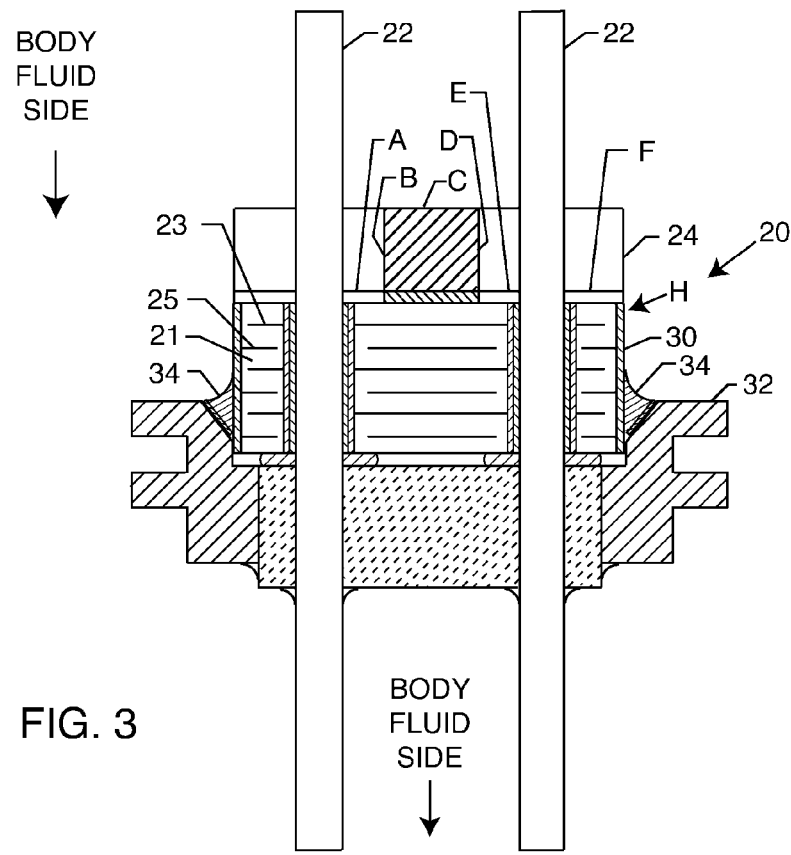
FIG. 3 is a cross-sectional side elevation view of the terminal assembly and mullion taken along line 3-3 of FIG. 2.
Figure 4:
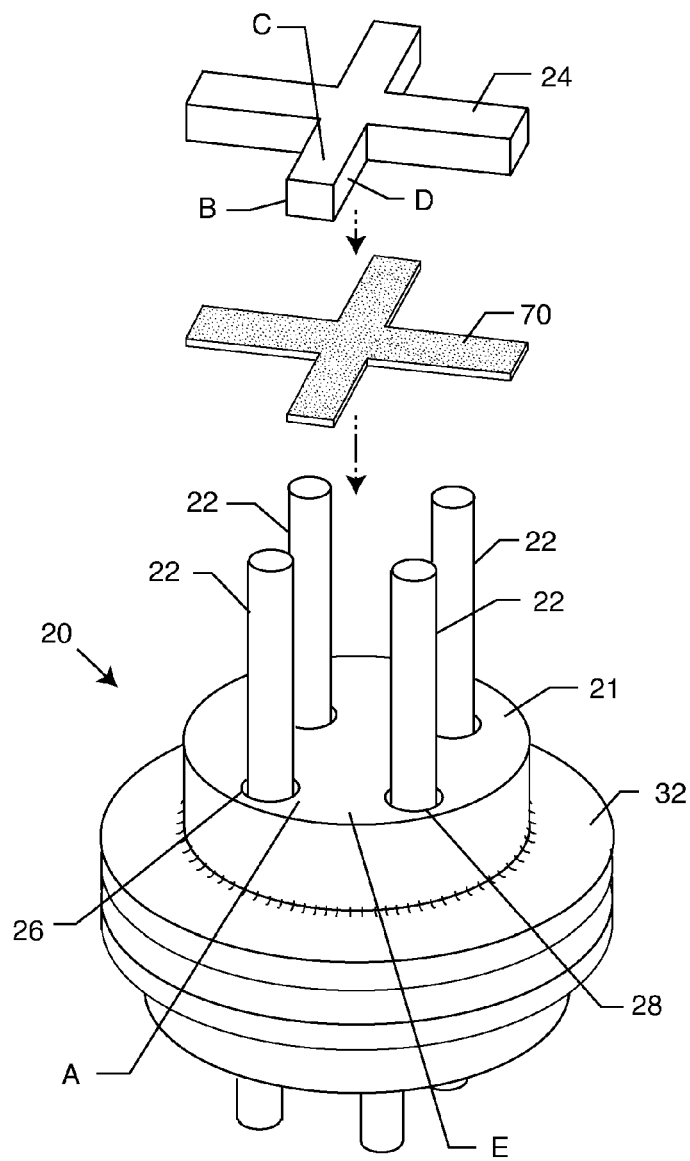
FIG. 4 is an exploded perspective view of the AIMD and mullion of FIG. 2.

As shown in the drawings for purposes of illustration, FIGS. 2-4 disclose an EMI feedthrough filter capacitor assembly 20 that includes a number of spaced-apart leadwires or terminal pins 22. There are four leadwires or terminal pins 22 illustrated in the figures although the actual number may vary from as few as one leadwire or terminal pin 22 to more than four. The distance the leadwires or terminal pins 22 are spaced apart from each other depends upon the particular medical device 10 and its application High voltage fields tend to arc across surfaces. As seen in the figures, a novel non-conductive mullion 24 has been added to the assembly 20 of the present invention. This greatly increases the surface path length between pins 22. Starting from the right edge of pin 22 on the left side of the terminal assembly 20 of FIG. 3, one can see that for an electric arc to follow the surface of the assembly 20, the electric arc would have to travel first along surface A, then up along surface B, across surface C, then down surface D, and across surface E to reach the point of opposite polarity on the left edge of pin 22 on the right side of the terminal assembly 20 of FIG. 3. In electrical engineering, this is called a tortuous path. In other words, the creepage distance from pin 22 to pin 22 has been significantly increased. This same feature (i.e., the mullion 24) can be on the body fluid side of the terminal assembly 20. This can be increasingly important to components exposed to body fluid in that tissue migration or even metal deposition can occur across such surfaces. The reason for this is that in a pacemaker, for example, there are electrical pulses present on the leads. There are also precious metal such as gold plating that could migrate or electroplate out in the presence of an electrolyte and voltage potential. Accordingly, an increased creepage path as illustrated in FIGS. 2-4 is easily applicable to all body fluid medical devices 10. This is better illustrated by referring to the isometric view shown in FIGS. 2 and 4. FIGS. 2 and 4 are isometric views of the upper surface of the terminal assembly 20. This is a quad polar device with an X-shaped or cross-shaped mullion 24 providing the required tortuous path. One can follow surfaces A, B, D, D, and E which greatly increases the clearance between the pin location holes 26 and 28.

The feedthrough filter capacitor 21 of the assembly 20 has a first set of electrode plates 23 conductively coupled to the terminal pins or leadwires 22, and a second set of electrode plates 25 conductively coupled to a housing, ferrule 32 or ground plane of the active implantable medical device 10. The non-conductive mullion 24 is disposed adjacent to the top surface of the capacitor 21 and relative to the terminal pin or leadwire 22 for increasing the creepage distance between the terminal pin or leadwire 22 and another conductive element, creating a tortuous path that increases resistance to arcing/flashover.

Referring once again back to FIG. 3, there is another way that a surface flash or high voltage arc over can occur. Starting at the right side of pin 22 and tracing across surfaces F and H, one can see that if pin 22 was at a positive high voltage relative to the capacitor outside diameter termination 30, then a voltage potential could occur across these surfaces. Referring to FIGS. 2-4, the ferrule 32, which is designed to be welded to the titanium housing of a pacemaker or other implantable medical device 10, is at ground potential in this example. Electrical connection material 34 connects mettalic ferrule 32 to the capacitor outside diameter metallization 30. Accordingly, the outside diameter metallization 30 is at the same potential as the ferrule 32. The capacitor and the mullion 24 can be partially housed within the ferrule 32.

Figure 5:
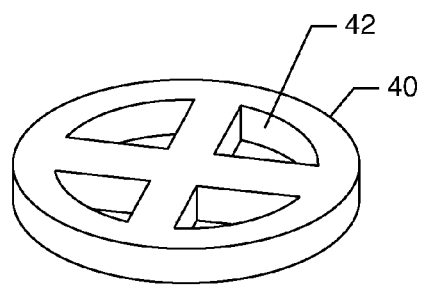
FIG. 5 is a perspective view of another embodiment of a mullion of the present invention.

In another embodiment, a disc-shaped mullion structure 40 is shown in FIG. 5. This mullion 40 has apertures 42 which define a central X-shape or cross-shape structure in the middle of the disc 40 that is similar to the mullion 24 of FIGS. 2-4. The apertures 42 may be various shapes including, without limitation, the pie-shaped apertures 42 shown in FIG. 5.

Figure 6:
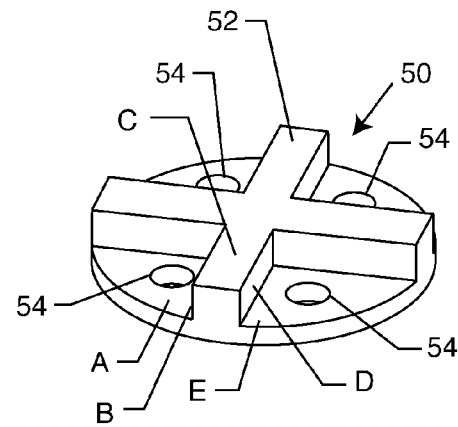
FIG. 6 is a perspective view of an additional embodiment of a mullion of the present invention.

In a further embodiment, a disc-shaped mullion structure 50 is shown in FIG. 6. that is similar to the mullion 40 of FIG. 5 except that a central X-shape or cross-shape structure 52 is not defined by apertures 54 in the mullion 50, but rather as an extension of the disc 50 that extends outwardly from surfaces A and E for separating the terminal pins or leadwires 22, which pass through the apertures 54, from one another. The extension 52 provides surfaces B, C and D for increasing creepage distance between the pins or leadwires 22.

Figure 7:
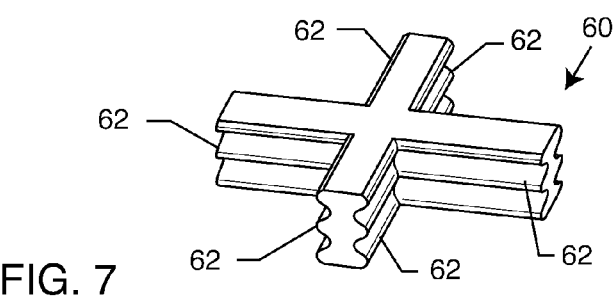
FIG. 7 is a perspective view of a further embodiment of a mullion of the present invention.

In an additional embodiment, an X-shaped or cross-shaped mullion structure 60, as shown in FIG. 7, would be preferred over a similar structure shown in FIGS. 2-4. The reason for this is that the mullion 60 of FIG. 7 includes a convoluted structure 62 similar to the insulator that would hang from a telephone power pole. These convolutions 62 greatly increase the creepage distance from pin 22 to pin 22 as the convolutions 62 increase insulator path length. A number of possible convoluted mullions 60 are possible, with an increased number of convolutions 62 increasing the creepage path between the opposing pins 22, for example, between pin location holes 26 and 28 of FIGS. 2 and 4.

Of course, in programmable implantable defibrillators, it is possible to have the can active. In other words, the ferrule 32 could be positive in reference to pin 22 which could then be negative and so on. However, in all cases it is desirable to have as much stand off distance as possible from pin 22 to pin 22 and from pin 22 to ground.

The mullion 24, 40, 50, 60 is bonded or adhesively connected to the top surface of the capacitor 21 of the terminal assembly 20. A thin layer of adhesive or adhesive-coated insulation washer 70 is disposed between the mullion 24, 40, 50, 60 and the capacitor 21 for connecting mullion 24, 40, 50, 60 and capacitor together. As outlined above, the mullion 24, 40, 50, 60 could also be adhesively connected to the body fluid side of the assembly 20 about the pins 22.

The mullion 24, 40, 50 60 can be composed of any suitable insulating material including, without limitation, plastic, epoxy, ceramic, polyimide, glass, FR4 or fiberglass or the like. The mullion 24, 40, 50 60 can be in various geometric shapes beyond those described above including, without limitation, rectangular, square or the like.

Although several different embodiments of the present invention have been illustrated and described in detail, various modifications may be made without departing from the spirit and scope of the invention. Accordingly, the invention is not to be limited, except as by the appended claims.

What is claimed is:

1. A feedthrough terminal assembly for an active implantable medical device, comprising:
   a conductive terminal pin or leadwire;
   a feedthrough filter capacitor having an outboard body fluid side, an inboard side, a first set of electrode plates conductively coupled to the terminal pin or leadwire, and a second set of electrode plates conductively coupled to a housing, ferrule or ground plane of the active implantable medical device; and
   a non-conductive mullion bonded to said inboard side of said feedthrough filter capacitor and relative to the terminal pin or leadwire for increasing creepage distance between the terminal pin or leadwire and another conductive element, creating a tortuous path that increases resistance to arcing/flashover.

2. The assembly of claim 1, wherein the active implantable medical device comprises a cardiac pacemaker, an implantable defibrillator, a congestive heart failure device, a hearing implant, a neurostimulator, a drug pump, a ventricular assist device, an insulin pump, a spinal cord stimulator, an implantable sensing system, an artificial heart, an incontinence device, a bone growth stimulator, a gastric pacemaker or a prosthetic device.

3. The assembly of claim 1, including a second conductive terminal pin or leadwire extending through the feedthrough filter capacitor wherein at least a portion of the mullion is disposed between the conductive terminal pins or leadwires.

4. The assembly of claim 1, wherein the mullion is adhesively connected to the capacitor.

5. The assembly of claim 1, wherein the capacitor is at least partially housed within a ferrule.

6. The assembly of claim 3, wherein the mullion comprises a disc having apertures through which the terminal pins or leadwires extend.

7. The assembly of claim 6, wherein the disc includes an extension for separating the terminal pins or leadwires from one another.

8. The assembly of claim 7, wherein the extension includes convolutions for increasing creepage distance.

9. A feedthrough terminal assembly for an active implantable medical device, comprising:
   a first conductive terminal pin or leadwire;
   a feedthrough filter capacitor having an outboard body fluid side, an inboard side, a first set of electrode plates conductively coupled to the first terminal pin or leadwire, and a second set of electrode plates conductively coupled to a housing, ferrule or ground plane of the active implantable medical device; and
   a non-conductive mullion bonded to said inboard side of the capacitor and relative to the terminal pin or leadwire for increasing creepage distance between the first terminal pin or leadwire and a second conductive terminal pin or leadwire extending through the feedthrough filter capacitor wherein at least a portion of the mullion is disposed between the conductive terminal pins or leadwires, creating a tortuous path that increases resistance to arcing/flash over.

10. The assembly of claim 9, wherein the active implantable medical device comprises a cardiac pacemaker, an implantable defibrillator, a congestive heart failure device, a hearing implant, a neurostimulator, a drug pump, a ventricular assist device, an insulin pump, a spinal cord stimulator, an implantable sensing system, an artificial heart, an incontinence device, a bone growth stimulator, a gastric pacemaker or a prosthetic device.

11. The assembly of claim 9, including an adhesive-coated insulation washer between the capacitor and the mullion.

12. The assembly of claim 9, wherein the capacitor is at least partially housed within a ferrule.

13. The assembly of claim 9, wherein the mullion comprises a disc having apertures through which the terminal pins or leadwires extend.

14. The assembly of claim 13, wherein the disc includes an extension for separating the terminal pins or leadwires from one another.

15. The assembly of claim 14, wherein the extension includes convolutions for increasing creepage distance.

16. A feedthrough terminal assembly for an active implantable medical device, comprising:
   a conductive terminal pin or leadwire;
   a feedthrough filter capacitor having an outboard body fluid side, an inboard side, a first set of electrode plates conductively coupled to the terminal pin or leadwire, and a second set of electrode plates conductively coupled to a housing, ferrule or ground plane of the active implantable medical device; a non-conductive mullion adhesively bonded to said inboard side of the capacitor and relative to the terminal pin or leadwire for increasing creepage distance between the terminal pin or leadwire and another conductive element, creating a tortuous path that increases resistance to arcing/flashover; and
   wherein the active implantable medical device comprises a cardiac pacemaker, an implantable defibrillator, a congestive heart failure device, a hearing implant, a neurostimulator, a drug pump, a ventricular assist device, an insulin pump, a spinal cord stimulator, an implantable sensing system, an artificial heart, an incontinence device, a bone growth stimulator, a gastric pacemaker or a prosthetic device.

17. The assembly of claim 16, including a second conductive terminal pin or leadwire extending through the feedthrough filter capacitor wherein at least a portion of the mullion is disposed between the conductive terminal pins or leadwires.

18. The assembly of claim 17, wherein the mullion comprises a disc including apertures through which the terminal pins or leadwires extend and an extension for separating the terminal pins or leadwires from one another, and wherein the extension has convolutions for increasing creepage distance.

19. The assembly of claim 16, wherein the mullion is adhesively connected to the capacitor by means of an adhesive-coated insulation washer.

20. The assembly of claim 19, wherein the capacitor and the mullion are at least partially housed within a ferrule.

21. The assembly of claim 1, including an adhesive-coated insulation washer between the capacitor and the mullion.

* * * * *